United States Patent
Murali

(10) Patent No.: US 10,271,768 B1
(45) Date of Patent: Apr. 30, 2019

(54) METHOD FOR DETERMINING REHAB PROTOCOL AND BEHAVIOR SHAPING TARGET FOR REHABILITATION OF NEUROMUSCULAR DISORDERS

(75) Inventor: Sanjai Murali, Somerset, NJ (US)

(73) Assignee: Jogohealth Inc., Bridgewater, NJ (US)

( * ) Notice: Subject to any disclaimer, the term of this patent is extended or adjusted under 35 U.S.C. 154(b) by 633 days.

(21) Appl. No.: 13/329,827

(22) Filed: Dec. 19, 2011

Related U.S. Application Data

(60) Provisional application No. 61/426,567, filed on Dec. 23, 2010.

(51) Int. Cl.
*A61B 5/00* (2006.01)
*A61B 5/11* (2006.01)
*A61B 5/0488* (2006.01)

(52) U.S. Cl.
CPC .............. *A61B 5/11* (2013.01); *A61B 5/1124* (2013.01); *A61B 5/0488* (2013.01)

(58) Field of Classification Search
CPC ....... A61H 1/0274–1/0237; A61H 2201/1215; A61H 2201/1635; A61H 2201/1642; A61H 2201/1659; A61H 2201/5043; A61H 2201/0184; A61H 2201/1238; A61H 2201/5023; A61H 2201/5035; A61H 2201/5038; A61H 2201/5058; A61B 5/11–5/16; A61B 5/7267–5/7475
See application file for complete search history.

(56) References Cited

U.S. PATENT DOCUMENTS

| | | | | |
|---|---|---|---|---|
| 5,277,197 A * | 1/1994 | Church | ................. | A61B 5/486 600/546 |
| 5,722,420 A * | 3/1998 | Lee | ........................ | A63B 24/00 482/4 |
| 5,810,747 A * | 9/1998 | Brudny et al. | ................ | 600/595 |
| 5,885,231 A * | 3/1999 | Cramer et al. | ................ | 600/595 |
| 6,270,445 B1 * | 8/2001 | Dean et al. | ...................... | 482/4 |
| 6,379,393 B1 * | 4/2002 | Mavroidis et al. | ............ | 623/25 |
| 6,413,190 B1 * | 7/2002 | Wood | ................... | A61B 5/1071 463/36 |
| 6,511,442 B1 * | 1/2003 | Lathan | ................... | G09B 23/28 600/595 |
| 6,774,885 B1 * | 8/2004 | Even-Zohar | .................. | 345/156 |

(Continued)

*Primary Examiner* — Christopher A Flory
*Assistant Examiner* — Shirley X Jian
(74) *Attorney, Agent, or Firm* — Snyder, Clark, Lesch & Chung, LLP

(57) ABSTRACT

A system for treating a patient with neurological disorders of movement includes a patient computing device for use in rehabilitative training and a sensor worn about a body part being rehabilitated. A healthcare computing device is used by a healthcare professional to assist remote patient rehabilitation by accepting input signals and determining for the patient a rehab protocol depending on selected parameters, and determining for the patient a behavior shaping target depending on selected parameters and the rehab protocol and behavior shaping target is communicated to the patient while the patient is undergoing rehabilitation. A plurality of remote health data sites and other public repositories of health data of patients undergoing rehabilitation following neurological events can be included. The remote computing device can include a data repository of publicly available patient data and patient data gathered by system of present invention.

18 Claims, 11 Drawing Sheets

(56) References Cited

U.S. PATENT DOCUMENTS

| | | | |
|---|---|---|---|
| 7,121,981 B2* | 10/2006 | Whitall et al. | 482/8 |
| 7,252,644 B2* | 8/2007 | Dewald | A61H 1/02 601/23 |
| 7,563,234 B2* | 7/2009 | Cordo | A61B 5/0488 600/595 |
| 7,725,175 B2* | 5/2010 | Koeneman | A61H 1/02 600/546 |
| 7,751,878 B1* | 7/2010 | Merkle | A61B 5/04 600/544 |
| 8,012,107 B2* | 9/2011 | Einav et al. | 601/5 |
| 8,062,129 B2* | 11/2011 | Pope | A63F 13/06 463/31 |
| 8,187,152 B2* | 5/2012 | Gravel et al. | 482/7 |
| 8,214,029 B2* | 7/2012 | Koeneman | A61H 1/02 600/546 |
| 8,262,541 B2* | 9/2012 | Gravel et al. | 482/7 |
| 8,359,123 B2* | 1/2013 | Tong | A61H 1/0237 600/546 |
| 8,437,844 B2* | 5/2013 | Syed Momen et al. | 600/546 |
| 8,585,620 B2* | 11/2013 | McBean | A61F 5/0127 600/546 |
| 8,768,428 B2* | 7/2014 | Clare | A61B 5/6833 600/382 |
| 8,926,534 B2* | 1/2015 | McBean | A61F 5/0127 601/24 |
| 2004/0267331 A1* | 12/2004 | Koeneman | A61H 1/02 607/49 |
| 2006/0079817 A1* | 4/2006 | Dewald | A61H 1/02 601/5 |
| 2007/0050715 A1* | 3/2007 | Behar | A61B 5/0002 715/706 |
| 2007/0282228 A1* | 12/2007 | Einav et al. | 601/33 |
| 2007/0299371 A1* | 12/2007 | Einav et al. | 601/5 |
| 2008/0058668 A1* | 3/2008 | Seyed Momen et al. | 600/546 |
| 2008/0071386 A1* | 3/2008 | McBean | A61F 5/0127 623/25 |
| 2008/0081692 A1* | 4/2008 | Pope | A63F 13/06 463/31 |
| 2008/0234781 A1* | 9/2008 | Einav et al. | 607/48 |
| 2008/0281633 A1* | 11/2008 | Burdea et al. | 705/2 |
| 2009/0062698 A1* | 3/2009 | Einav et al. | 601/5 |
| 2009/0147991 A1* | 6/2009 | Chau | 382/103 |
| 2009/0171227 A1* | 7/2009 | Dziubinski et al. | 600/516 |
| 2009/0171233 A1* | 7/2009 | Lanfermann | A61B 5/0488 600/546 |
| 2009/0171417 A1* | 7/2009 | Philipson | A61N 1/36003 607/48 |
| 2009/0227925 A1* | 9/2009 | McBean | A61F 5/0127 602/16 |
| 2009/0326406 A1* | 12/2009 | Tan | G06F 3/015 600/546 |
| 2010/0179453 A1* | 7/2010 | Schweighofer | A61B 5/1118 600/595 |
| 2010/0198115 A1* | 8/2010 | Koeneman | A61H 1/02 601/5 |
| 2010/0293115 A1* | 11/2010 | Seyed Momen | 706/12 |
| 2011/0082397 A1* | 4/2011 | Alberts | 601/26 |
| 2012/0142416 A1* | 6/2012 | Joutras | G09B 19/0038 463/36 |
| 2014/0142474 A1* | 5/2014 | McBean | A61F 5/0127 601/33 |
| 2014/0303508 A1* | 10/2014 | Plotnik-Peleg | A61B 5/744 600/483 |

* cited by examiner

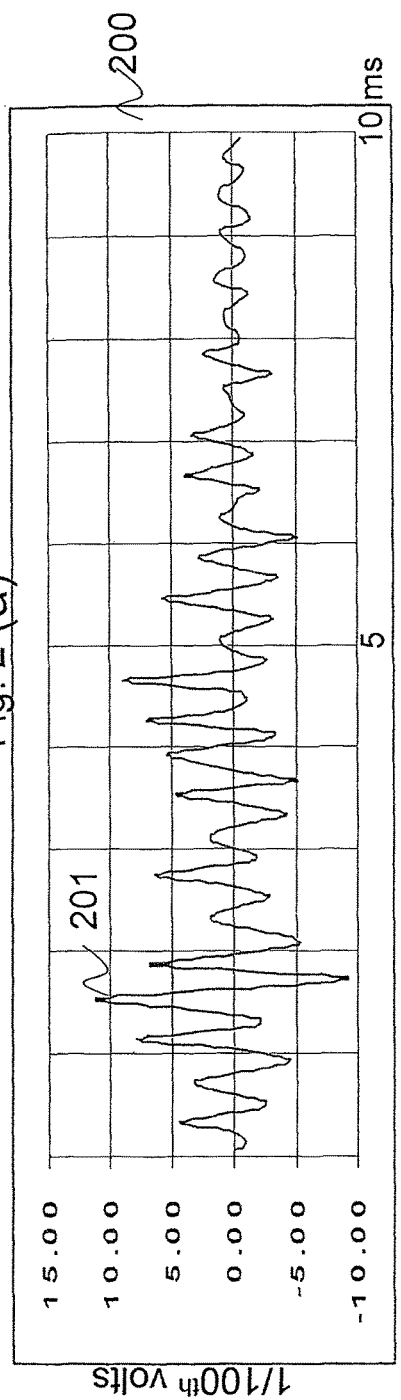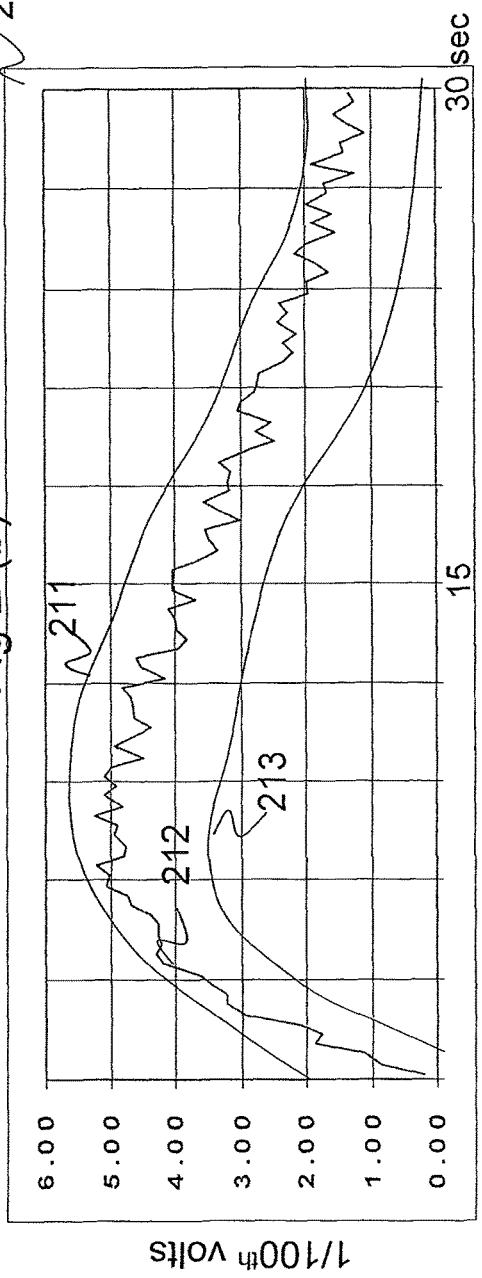

20 – Representative embodiment of Wireless bandaid EMG sensor - plan view

21 – Casing - housing sensor elements

22 – Bandaid fabric – non adhesive side

23 – Sensor element – skin side 23a,b,c – Sensor electrode contact points

24 – Sensor casing, elevation view

25 – self adhesive peel off before use

30 – a portable wireless patient computing device
31 – camera
32b – EMG output
32a – Target boundary
33 – Target boundary
34 – Touch screen display
35 – Video stream from remote healthcare professional
36a,b,c,d,e – GUI, software control elements
37 – Microphone
38 – On/Off button
39a,b – USB port
39c – Speaker Fig 9
(a)

Patient's Name: _____ Age: _____ Date: _____

Diagnosis: _____ Date of Onset: _____

Past Medical History: _____

Social History: _____

Environment: _____ Equipment: _____

Mental Status: _____ Discharge Plans: _____

Subjective: _____

Objective: Vital Signs: BP _____ HR _____ Respirations _____ Hearing _____

| Vision _____<br>Speech _____<br>Sensory _____ | ROM | | STRENGTH or<br>Pathol. Synergy | | OTHER: Pain, edema, skin integrity.<br>Sensory deficits, comments. |
|---|---|---|---|---|---|
| | (R) | (L) | (R) | (L) | |
| Trunk Mobility | | | | | |
| Hip Flexion | | | | | |
| Extension | | | | | |
| Abduction | | | | | |
| Adduction | | | | | |
| Int. Rotation | | | | | |
| Ext. Rotation | | | | | |
| Knee Flexion | | | | | |
| Extension | | | | | |
| S.L.R. | | | | | |
| Ankle DorsiFl | | | | | |
| Plantar Fl | | | | | |
| Inversion | | | | | |
| Eversion | | | | | |
| Shoulder Flexion | | | | | |
| Extension | | | | | |
| Abduction | | | | | |
| Int. Rot. | | | | | |
| Ext. Rot. | | | | | |
| Elbow Flexion | | | | | |
| Extension | | | | | |
| Forearm Supin. | | | | | |
| Pronation | | | | | |
| Wrist Flexion | | | | | |
| Extension | | | | | |
| Ulnar/Rad Dev | | | | | |
| Finger Flexion | | | | | |
| Extension | | | | | |
| Thumb Web space | | | | | |

Fig 9 (b)

PATIENT NAME: _____ DATE: _____

| Functional Status | Level * | Comments/equipment | BALANCE | COMMENTS |
|---|---|---|---|---|
| EATING | | | STATIC-SIT | |
| GROOMING | | | DYNAMIC-SIT | |
| BATHING | | | STATIC - STAND | |
| UE DRESSING | | | DYNAMIC -STAND | |
| LE DRESSING | | | POSTURE | |
| TOILET HYGIENE | | | SITTING | |
| BED MOBILITY | | | STANDING | |
| TRANSFER TO BED/CHAIR | | | AMBULATION LEVEL SURFACE | |
| TRANSFER TO COMMODE/TOILET | | | STAIRS, CURBS, RAMPS | |
| TRANSFER TO TUB | | | UNEVEN SURFACE | |

* FIM SCORE (FOR FUNCTIONAL STATUS)　　　1- Dependent 75-100%　　2 - Max. Assist 50-74%
　　3- Mod. Assist 25-49%　　4- Min. Assist < 25%　　5 - Supervision　　6 - Modified Indep.　　7 - Indep

| GAIT ANALYSIS: Include assistive devices and orthotics (What does patient have, what does patient need?) |
|---|
| |
| |
| WHEELCHAIR MANAGEMENT & PROPULSION: |
| COORDINATION AND MOTOR CONTROL: |
| |
| ENDURANCE: |
| HOMEBOUND STATUS: |
| REHAB POTENTIAL: |

PROBLEMS:　　　　　　　　　　　　　PLAN:

| 1. |
|---|
| 2. |
| 3. |
| 4. |

GOALS:　　　　　　SHORT TERM　　　　　　LONG TERM

| 1. |
|---|
| 2. |
| 3. |
| 4. |
| 5. |

Fig 10

| | Condition | Rehab Protocol | Efficacy | Population | Clinical Studies |
|---|---|---|---|---|---|
| | 901 | 902 | 903 | 904 | 905 |
| | C1 | RP2, RP3 | x% | P2 | CS1, CS2, CS3 |
| | C2 | RP1, RP4 | y% | P1 | CS4, CS5 |

900

METHOD FOR DETERMINING REHAB PROTOCOL AND BEHAVIOR SHAPING TARGET FOR REHABILITATION OF NEUROMUSCULAR DISORDERS

FIELD OF INVENTION

The present invention is directed towards providing a means for delivering rehab intervention from a remote therapist to a home based patient who requires rehab therapies to recover deficits in neuromuscular functionality brought about by a neurological episode such as stroke, traumatic brain injury, spinal cord injury, and in general any neuromuscular disorder.

BACKGROUND OF THE INVENTION

Using instructional techniques, rehab interventions seek to maximize the potential for independent living for individuals who have suffered insults (or diseases), injuries to the central or peripheral nervous system, or other abnormalities of the neuromuscular system. In prior art these instructional techniques required that individuals present themselves to a caregiver (rehab provider) to receive and train in order to recover neuromuscular functionality. Various studies show that the individuals who are able to physically present themselves to a rehab provider are a minority compared to those who require such care. A vast majority of such individuals are confined to a home setting and lack the support structure to travel to a caregiver in order to receive rehab therapies.

The measurement, recording, and study of the intrinsic properties of skeletal muscles, or electromyography (EMG), has been used for over 100 years as a diagnostic modality in order to determine the nature of muscle dysfunction either as a result of injury to the nervous system or abnormality of muscle structure. In addition to diagnostics, EMG is also used as a therapeutic modality.

Research has shown that due to neural plasticity, the healthy parts of the brain gain the ability to perform functions lost due to neurological insults and injury, by repeated training through physical exercises. This is analogous to the experiment performed by the Russian scientist—Pavlov. Pavlov demonstrated that his dog could be trained by ringing the bell and presenting a bone to the dog. After repeated training, the dog salivates on hearing the bell—without a bone in front. This is called conditioned reflex wherein the dog is trained to correlate the ringing of a bell to the presence of a bone. In neuroscience parlance, this is referred to as instrumental conditioning.

The system of present invention works on a similar principle. A target is set for the patient on a computer screen such that the patient expends effort to bring the effort graph to coincide or reach the target point (or target graph) set by a healthcare professional—for example, a physical therapist or a occupational therapist.

There are a number of existing rehabilitation systems (computer based) that employ EMG towards a therapeutic modality for rehabilitation of neuromuscular conditions.

The existing rehabilitation systems (computer based) can be classified into EMG monitors, neuro-robotic rehab devices, functional electric simulation devices, and motion sensing rehab systems. These devices are typically expensive and are not designed for patient's ease of use in a home setting. Furthermore, these devices currently do not support predictive analysis by examining a) patient's history, b) comparing data of similar patients with similar prognosis, either in its own repository or publicly available data under such sites as Healthvault, and such other data and future data available from sites such as CMS (center for Medicare and Medicaid Service)

Existing rehabilitation systems are therefore limited in scope with respect to efficacy and personalization to a patient's unique condition. Furthermore, existing systems are expensive and don't lend themselves to ease of use in a patient's home setting.

The system of present invention addresses these issues through a method for determining the rehab protocol and behavior shaping target by leveraging patient's physiologic measures, and data available from other sources.

SUMMARY OF INVENTION

A system for treating a patient with neurological disorders of movement includes a patient computing device for use in rehabilitative training and a sensor worn about a body part being rehabilitated. A healthcare computing device is used by a healthcare professional to assist remote patient rehabilitation by accepting input signals and determining for the patient a rehab protocol depending on selected parameters, and determining for the patient a behavior shaping target depending on selected parameters and the rehab protocol and behavior shaping target is communicated to the patient while the patient is undergoing rehabilitation. A plurality of remote health data sites such as Healthvault, Healthdata.gov, and other public repositories of health data of patients undergoing rehabilitation following neurological events can be included. The remote computing device can include a data repository of publicly available patient data and patient data gathered by system of present invention. The sensor can be a wireless bandaid sensor capable of measuring and transmitting electromyography, capable of measuring and transmitting joint angle, capable of measuring and transmitting speed of motion and other physiological signals to patient computing device. The patient can receive rehab therapies from remote healthcare professionals. The patient can perform rehabilitation protocols in a home setting unsupervised by the remote healthcare professional.

The invention is a method for determining rehab protocol patient evaluation by a healthcare professional, evaluation of input into expert system, wherein the healthcare professional selects an option: supervised learning or unsupervised learning or probabilistic learning. An expert system outputs a choice of rehab protocols, and a healthcare professional selects a rehab protocol or overrides rehab protocol or modifies rehab protocol.

Furthermore, the method for dynamically determining behavior shaping target includes a patient starting the rehab protocol, a system of present invention capturing patient output comprising of EMG response, joint angle, speed of motion. The healthcare professional selects one of the following modes of deriving behavior shaping target: patient history, or comparison with similar patients, or manual. Fuzzy logic algorithms determine behavior shaping target, and the healthcare professional adjusts or over rides to manually create behavior shaping target.

The invention is a method for capturing effectiveness of a the rehab protocol by analysis of patient EMG response, physiological parameters, and improvements in the following: Barthel's index, Fugl Meyer scores, and FIM, score, and a method for displaying rehab protocol effectiveness of said rehab protocol against a reference set of patient population such that healthcare professional can determine a treatment regimen that is most effective. A virtual reality representation of the rehab protocol can be provided; the virtual reality representation showing difference of target and achievement; virtual reality representation showing EMG response (amplitude) variation with appropriate color scheme on virtual body part.

The present invention comprises a system of hardware elements and software elements which improves access, delivery, and efficacy of rehabilitation administered to individuals suffering from neurological disorders of movement. The system can be employed to remotely or locally monitor progress and/or control the rehabilitative protocols of a person undergoing retraining and/or rehabilitation specific to his or her dysfunction or deficit.

The system of the present invention can be used for a variety of applications involving central nervous system (CNS) and peripheral nervous system insults, diseases, injuries or dysfunctions. CNS insults may include: stroke, cerebral palsy, trauma, incomplete spinal cord injury, Parkinson's, back pain, and multiple sclerosis. Injuries or insults to the peripheral nervous system include facial paralysis, brachial plexus injury or injury to the lumbar plexus. In general, the present invention can be used for neuromuscular rehabilitation, and orthopedic rehabilitation.

In the representative embodiment, the present invention links a healthcare professional to a patient via the internet. The present invention includes an interactive multimedia format that allows high quality healthcare to be provided to patients in remote locations, both in the US and throughout the world.

In accordance with the present invention, a wireless BANDAID® type flexible adhesive sensor (sensor) that is worn by the patient suffering from neurological trauma, spinal cord or other nerve damage including stroke or neuromuscular disorder or a patient requiring general rehabilitation services or strength increases includes a sensor which senses an electrical signal at a muscle which is proximate the body part and a patient computing device which communicates with the sensor and displays the signal transmitted by the sensor. The sensor senses or otherwise determines the physiological signals which is then transmitted to patient computing device; physiological signals include those of muscular and brain functions (e.g. EMG, EEG), accurate and objective measures of movement, angle of movement, speed of movement, and other patient responses. The sensor may have ability to provide tactile sensations such as vibrations or mechanical pressure. The sensor may include an integrated processor which utilizes signals produced by the sensor or alternatively the processor may be separate from the sensor—patient computing device has the ability to receive wireless signals encapsulating patient physiological data for further processing. A representative embodiment of patient computing device is capable of the following: capturing audio and video information of the patient as well as display video information and output audio; receive audio and video information transmitted by healthcare professional; receive any computing signal that signifies a modification, selection, or update to a rehab protocol or any data set pertaining to the patient; running computational algorithms that take patient physiological signals as input and derive behavior shaping target graph; connection to the internet; connection to a remote healthcare professional; connection to a remote data repository to draw relevant data to compute predictive algorithms for determining rehab protocol as well as behavior shaping target. It will be understood by those of ordinary skill in art that computation of algorithms can happen remotely on the cloud or on the patient computing device.

Other representative embodiments of patient computing device include wireless smartphones, wireless capable TV display units that can work with a smartphone, and custom built patient computing device that have the aforementioned characteristics and capability in addition to others.

In a representative embodiment, a healthcare professional uses a PC that is capable of connecting to the internet, and has hardware and software components for audio and video communication. Other representative embodiments of devices used by healthcare professionals include wireless smartphones with capability for audio and video communication.

The healthcare professional logs onto a server on the Internet to access software programs necessary to connect to a remote patient and deliver therapy. Tools necessary to interpret, modify, and adjust therapy delivery is available as control elements in the software application that the healthcare professional uses to deliver rehab therapies to the remote patient. Prior to start of rehab, the healthcare professional has the ability to input various evaluation measures that capture the present status of the patient. Expert systems and predictive algorithms use this data and other relevant data from public and private sites to determine a rehab protocol. The healthcare professional has the ability to accept, modify this rehab protocol or custom create a rehab protocol from heuristic information.

In accordance with the present invention, a patient logs on to a server on the internet to be connected to a remote healthcare professional in order to receive rehab therapy. Patient wears sensors that communicate with the patient computing device or PC. An EMG sensor is fixed to an elastic bandaid form factor such that the sensor is coupled with at least one muscle of the person. In response to the person attempting to move the body part, the sensor senses a surface EMG signal of the muscle. The patient computing devices determines a desired behavior shaping target from the EMG signal, through the use of behavior shaping algorithms. In one embodiment, the behavior shaping target is determined via EMG sensors, force sensors, velocity sensors, position sensors or some combination thereof. In some embodiments, the sensor can be placed inside a garment worn as a sock, glove, or vest. The sensor element is lightweight, unobtrusive and doesn't impede the movement of the person wearing the sensor. The sensor is so placed on a muscle such that it doesn't fall away from the body of the person during the course of motion intended for rehabilitation, and is in constant contact with the muscle. In certain embodiments, restraining mechanism is used to hold the sensor in position on the muscle. In typical embodiments, the sensors are so placed in order to gain EMG signals from agonist and antagonist muscle groups. A plurality of sensors is used depending on the rehabilitation goal and protocol.

Physiologic and other movement data from the patient is obtained from various transduction elements at multiple anatomical sites, converted into PC compatible data, and is further transformed or converted in to data that represents a determination of the patient's muscular movement or response. This information may then be used to control a meaningful display of the underlying information on the patient computing device (monitor) such as movement of a virtual representation of part of a human body (e.g., face, arm), an avatar that represents the ideal sequence of motion or simply represent the motion of the patient wearing the sensor, or possibly generate a sound or vibration having equivalent representation of the movement response. It will be appreciated by those skilled in art that the patient can undergo rehab therapies from the comfort of the home. The visual target in the form of behavior shaping target allows the patient to exercise such that effort exerted by the patient corresponds to the target graph displayed. Various forms of tactical stimuli is provided such as visual, or sound, or vibration on the sensor, to indicate either achievement or non achievement of target. Patients respond well when motivated by target and rewards for achieving the target. The system of present invention provides features to enable motivation by a system of target and rewards.

In accordance with the present invention, a video demonstration of the said rehab protocol will be displayed on the patient computing device to enable the patient to observe and emulate the exercise. The remote healthcare professional and the patient or the patient's care giver communicate over the bidirectional audio and video link enabling the healthcare professional to communicate and demonstrate instructions to the patient. A virtual reality representation of the patient's movement, an avatar, is displayed to help correlate patient movement to exercise protocol as well as the said behavior shaping target. It will be apparent to those skilled in art, the benefits this will accrue to the patient, and the motivation it brings to help a patient continue ongoing rehab.

The system of present invention both augments strength and can accelerate rehabilitation in people who have suffered from neurological trauma or neuromuscular disorders, or a general loss of strength.

BRIEF DESCRIPTION OF THE DRAWINGS

The aforementioned invention, concepts comprising the invention, and the manner of use of the invention may be more fully understood from the following detailed description of the drawings, in which:

FIG. 2 represents a raw EMG signal and a corresponding rectified EMG signal as well as the behavior shaping target derived from algorithms.

FIG. 9 is a representative embodiment of a patient evaluation chart.

FIG. 10 is a representative embodiment of a rehab protocol efficacy compared against patient condition, patient population, with reference to relevant clinical studies

DETAILED DESCRIPTION

Figure 1:
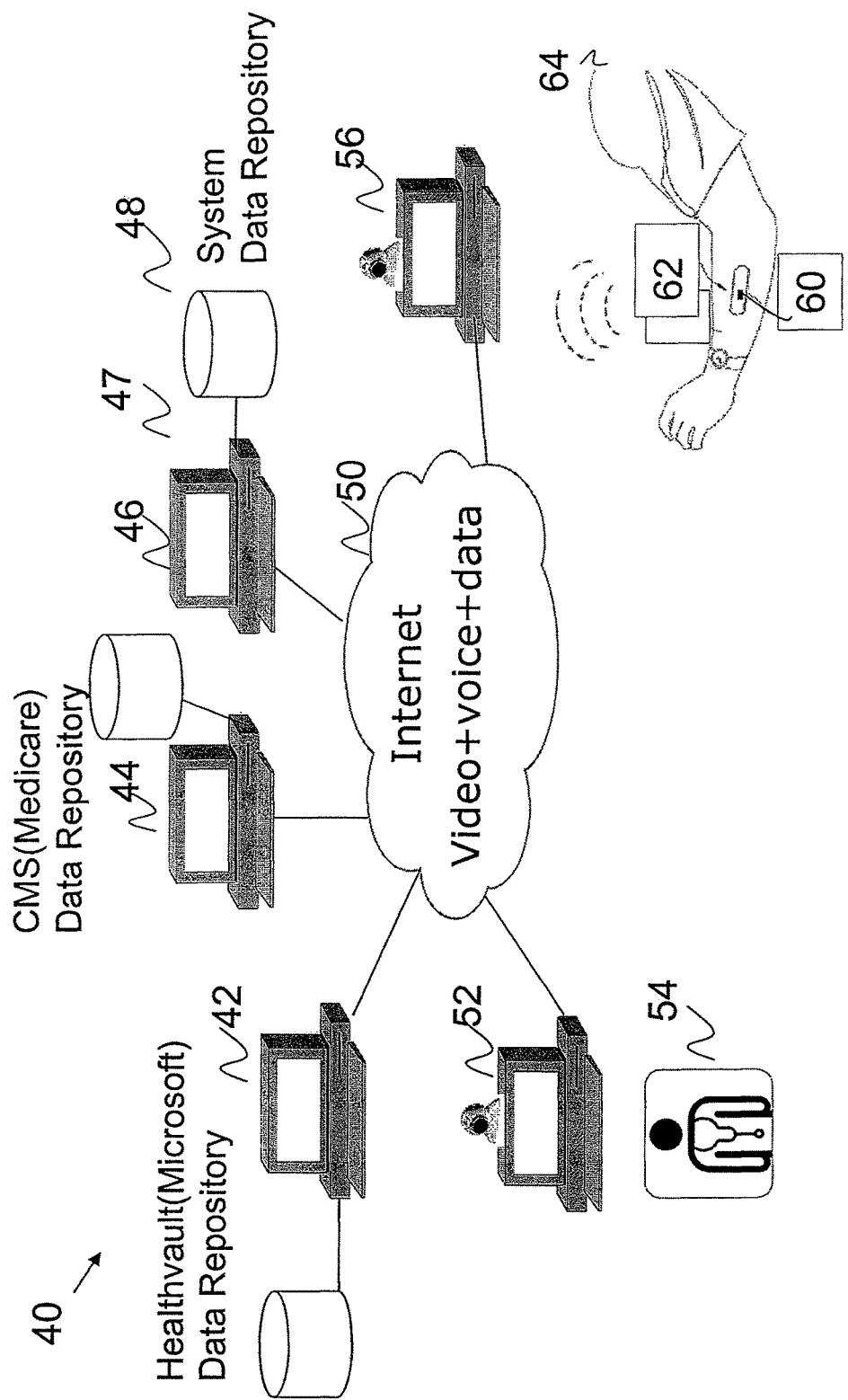
FIG. 1 is a diagrammatic view of the proposed system and components used for determining rehab protocol and behavior shaping target for rehabilitation of neuromuscular disorders.

Referring to FIG. 1, a representative embodiment illustrated by the organization of systems (architecture) required to deliver the rehab intervention comprising the present invention. A wireless bandaid sensor 62, is worn by the patient 64 who has lost the ability to normally bend or move an arm, leg, or body part. It should be understood that although the wireless bandaid sensor shown in FIG. 1, is applied to the arm, the device (wireless bandaid sensor) or suitably adapted variant can be worn on the leg or any body part that requires rehabilitation or strengthening. Sensor element 60 consists of sensor electrodes and electronics required for measuring the following: EMG, speed of motion, angle of motion, various physiological measures, and motion artifacts. Sensor element 60 also consists of required networking gear required to transmit aforementioned physiological measures through various wireless networking protocols and standards such as WiFi, Bluetooth, ANT, Zigbee; besides any proprietary wireless networking protocol required for transmission of physiological measures to the patient computing device 56. It will be appreciated by those of ordinary skill in the art that a variety of configurations are possible to transmit physiological measures (data), compute such signals with algorithms residing in a remote computing device 47 or a locally resident patient computing device 56. In this representative embodiment, the remote computing device 47, CMS data repository 44, Microsoft Healthvault 42, computing device used by healthcare professional 52, are connected to the internet 50.

Figure 3:
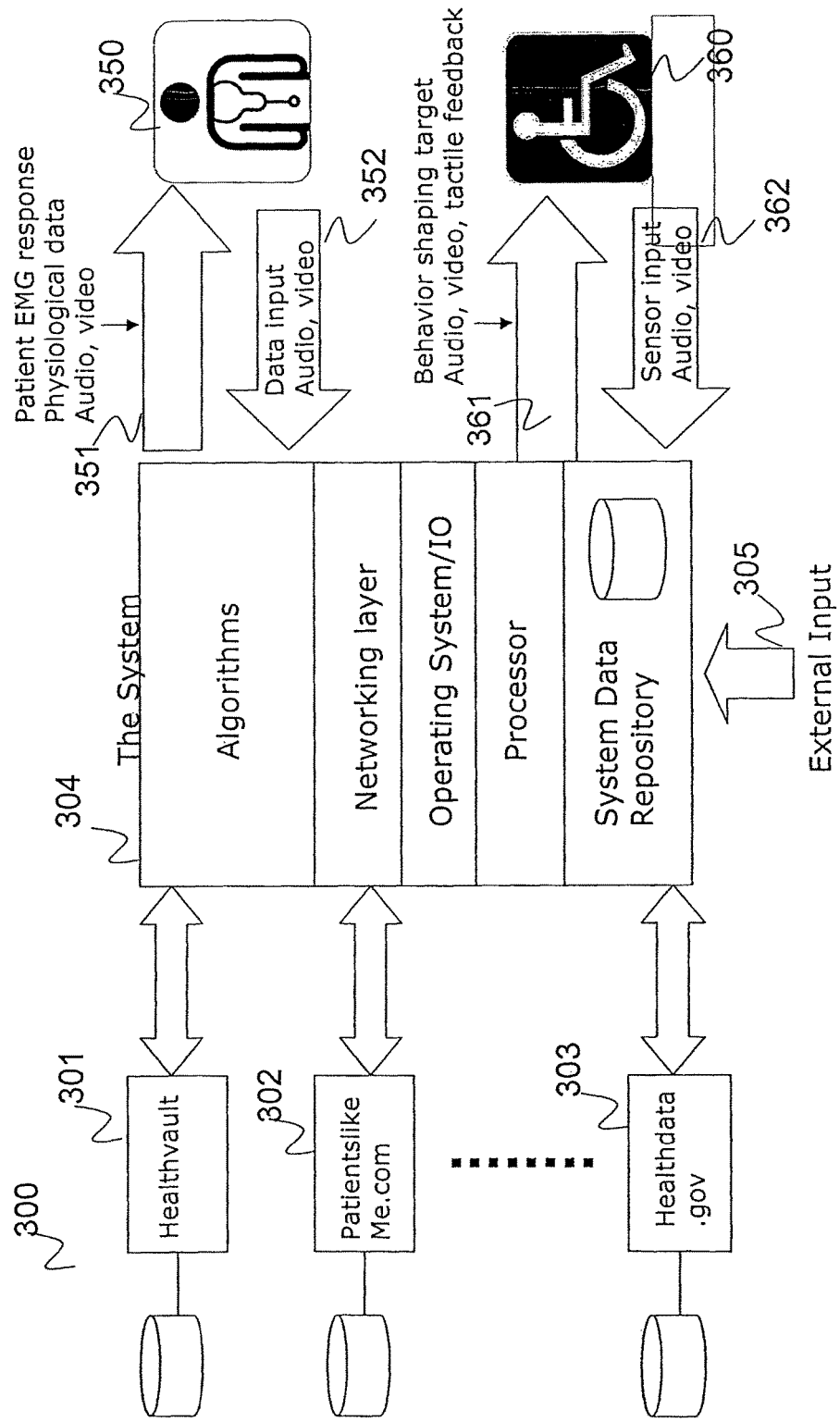
FIG. 3 is a diagrammatic view of various components of the system and exchange of data amongst the constituent components.

In FIG. 3, a system view of the system of the present invention is shown in 300. The system 304 provides for data storage of normalized patient data obtained from a variety of external public sources such as Healthvault 301, Patientslikeme.com 302, Healthdata.gov 303. It will be apparent to those of skill in art that the system of present invention can leverage a variety of such publicly available data repositories. Furthermore, the system 304 provides for execution algorithms necessary for determining rehab protocol, and behavior shaping target. The system 304 has its own processor and networking connectivity and means to receive external input 305 for administrative purposes. It will be apparent to those of ordinary skill in the art that the system 304 is a representative embodiment of a networked server. The healthcare professional 350 and the patient 360 interact with the help of the system 304. The healthcare professional receives patient EMG response, including other patient physiologic output, audio and video in 351. The healthcare professional's output 352 includes control settings, manual adjustments to rehab protocol, behavior shaping target, as well as audio and video. The patient 360 receives rehab protocol, behavior shaping target, healthcare professional's audio and video output, video of virtual reality representation, tactile stimulus in input 361. Output 362 captures signals transmitted by sensors worn by the patient as well as audio and video of the patient.

It will be apparent to those of ordinary skill in art that a variety of data repositories can be leveraged for computing the algorithm for determining the rehab protocol and the behavior shaping target. Each of the components of this representative embodiment is described in the following paragraphs.

Band Aid Sensor

Figure 6:
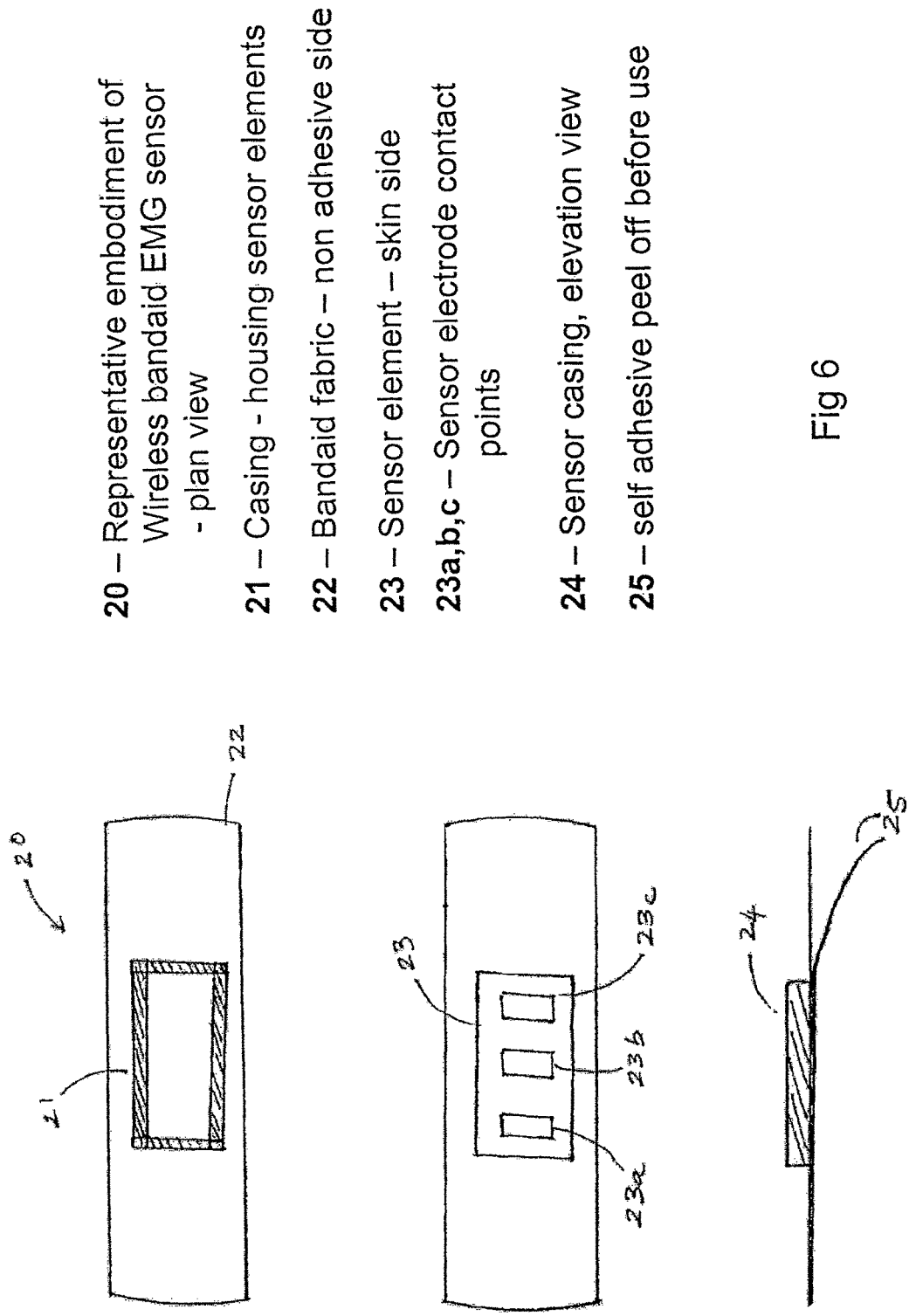
FIG. 6 is a representative embodiment of a wireless EMG sensor.

In the representative embodiment of wireless bandaid sensor 20 shown in FIG. 6; a self adhesive paper 25 is peeled off before the sensor is placed on the skin surface. It should be understood by those skilled in art that electrodes 23a, 23b, 23c need to make contact with skin surface proximate the muscle groups being rehabilitated or strengthened—for example, the agonist and antagonist muscle groups such as biceps and triceps. Furthermore, it will be understood by one of ordinary skill in the art that FIG. 6 shows various views of the bandaid sensor—top side, under side, and side view. Sensor electronics are housed in 21, skin side of the sensor electronics are shown in 23. 24 shows the height of the sensor electronics enclosure relative to the bandaid housing.

Figure 7:
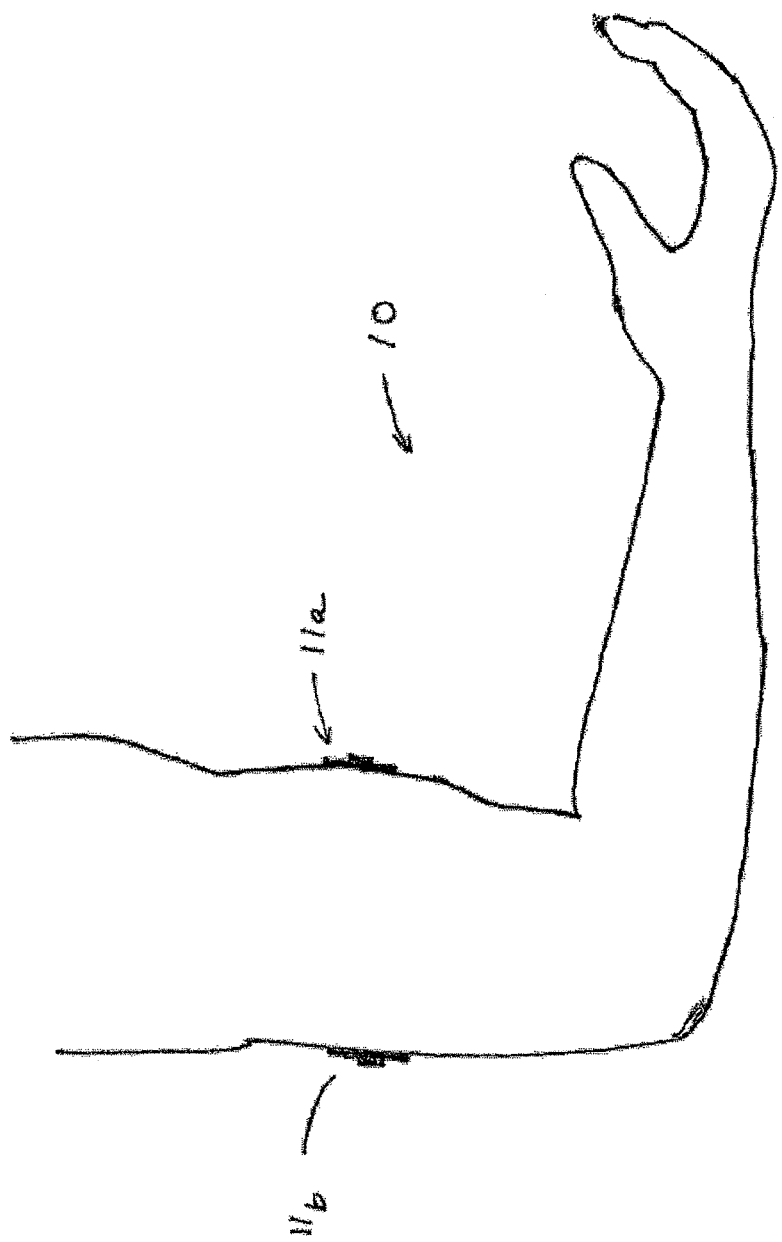
FIG. 7 is a diagram of wireless EMG sensors used on biceps and triceps.

Although one representative embodiment is shown in FIG. 6 and FIG. 7, it will be appreciated by one of ordinary skill in the art that many suitable variants are required depending on the actual need of the patient. Some embodiments may use a sock type housing for the sensor, or elastic band that flexes with contraction and stretching of muscle, or zip type fasteners adjacent to a cloth housing the sensor that ensures a snug fit; buckle type fasteners, hook and loop type fasteners; or friction type fasteners or some combination thereof that holds the sensor proximate to the body part and muscle being rehabilitated or strengthened.

In one particular embodiment, the sensors 11a and 11b (FIG. 7) are provided as non-invasive EMG sensors. Utilizing EMG sensors having relatively stiff electrodes contact pads contributes to the occurrence of motion artifacts. The reason is that the electrode contact pads do not bend synchronously with the body part as it changes shape during motion. This issue is addressed by appropriate housing of the sensor such that the sensor is proximate the body part under conditions expected during rehabilitation. The EMG sensors can be augmented by built-in signal processing elements such as filters and amplifiers to offset any issues associated with weak signal pickup from patient's body. In addition, appropriate indications such as flashing LED lights or software driven notification will help to alert the patient or healthcare professional about the need to adjust the sensor in the event of a weak or erroneous signal.

In other embodiments, the sensors 11a and 11b(FIG. 7) may be provided as invasive EMG sensors. In some other embodiments, additional sensors may be provided such as speed of motion (velocity) sensors, joint angle sensors, force sensors, etc. The input from these sensors will be required to measure and improve rehabilitation outcomes. The software algorithms compute rehab protocols and behavior shaping targets from these measures and additional measures which will be described later. In some instances, it may be desirable for the sensor to deliver a signal, a stimulus, to the muscle (proximate body part)—especially in a stroke patient, for example.

In some embodiments a plurality of sensors may be provided as per the requirements of rehabilitation. A sensor may also be provided at a location on patient's body that is not directly being rehabilitated—such sensors may be necessary to estimate compensatory mechanisms and thus derive better evaluation leading to better rehabilitation outcomes.

In some embodiments, sensors of multitude of form factors may be deployed depending upon the location of deployment as well as the rehabilitation requirements. Lower back pain, for example, requires sensor of such form factor that can be placed in the lower back region while maintaining a snug fit (contact) with the proximate body part or muscle. It will appreciated by those skilled in art that rehabilitation following orthopedic surgery, plastic surgery, can use a diagnostic and therapeutic modality employing the said plurality of sensors along with the software for determining rehab protocol and behavior shaping target to be described below.

There are numerous other conditions wherein the sensors described above in tandem with the software for determining rehabilitation protocol and behavior shaping target can be used to achieve the desired rehabilitation outcome. These conditions include but are not limited to Cerebral Palsy, Traumatic Brain Injury, Fibromyalgia, Parkinson's, amongst other neurological and physiological conditions where rehabilitation of the neuromuscular system is deemed necessary. As stated before, the ensemble of sensors and software can be used for strengthening purposes.

In Summary, sensors 11a and 11b may be provided as any type of invasive or non-invasive sensor capable of sensing information of the type required to appropriate signals for the determination of rehab protocol and behavior shaping target to be described below. In some instances, the sensors may be wired to the patient (as opposed to being wireless). The particular type of sensor to select for a particular application depends on a number of factors including but not limited to the type of signal that must be detected, the characteristic of the signal to be detected, the reliability of the sensors, sensitivity of the sensors and the cost of the sensors, the location on the body where the sensor must be placed, the strength of the output signal, battery life requirements, ease of use requirements such as repeated use or disposable as the case may be, the requirements of rehabilitation or strengthening as the case may be, and the operating environments in which the sensors will operate.

Figure 8:
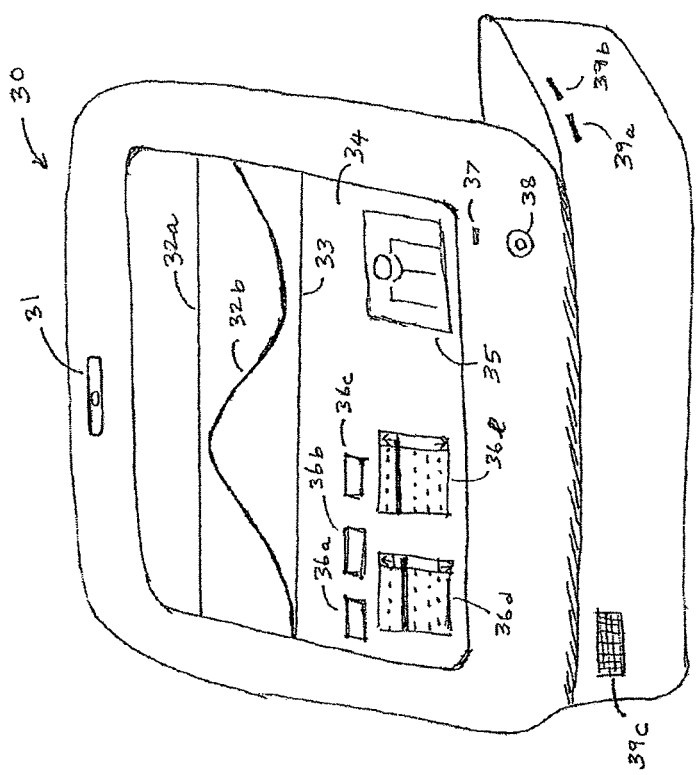
FIG. 8 is a diagrammatic representation of a representative embodiment of a patient computing device.

Sensors communicate with a Patient Computing Device, a representative embodiment 30 is shown in FIG. 8, which has its own processing module (not shown) having at least one processor (not shown), DSP module (not shown), and at least one data storage unit. The processor is adapted to execute software stored in the data storage unit, analyze patient data, display results of the analysis, amongst other things. Alternatively, it will apparent to those of ordinary skill in the art that Patient Computing Device 30 can act as a client with a bulk of the data processing and computation done remotely on a server connected to the internet. Patient Computing Device 30 supports communication through a variety of wireless interfaces such as Bluetooth, Zigbee, WiFi, infrared, and other propriety wireless transmission/receiver protocols. Patient Computing Device 30 also supports wireline networking interfaces such as Ethernet, data communication interfaces and ports such as USB 39a and 39b. Although not shown in FIG. 8, it will be appreciated by those of skill in the art that Patient Computing Device 30 has a port for charging its rechargeable battery; furthermore, such devices as routers, modems, hubs which may be necessary to achieve a network connection is also not show in FIG. 8. It will be understood by those skilled in art the ensemble of devices necessary to connect the Patient Computing Device 30 to the internet as well as to the wireless bandaid sensor. When necessary, suitable adapters can be used to wire the sensors to the USB ports 39a, 39b in FIG. 8. Patient Computing Device 30, also supports a touch screen interface 34, microphone 37, webcam 31, on/off switch 38, speaker 39c, and network protocols and interfaces such that the Patient Computing Device 30 can connect to the internet via WiFi, Cable Modem, as well as broadband wireless cellular interfaces such as 3G/4G. Patient Computing Device 30 may also include one or more audio input/output devices such as speakers, microphones, sirens, buzzers, etc., adapted to produce an audible message to patient. Patient Computing Device 30 may also include suitable adapters (not shown) that produce mechanical vibrations such that it may deliver a corresponding tactile sensation to patient to communicate either attainment of goal or otherwise falling short of the goal.

It will be understood by those of ordinary skill in the art that Patient Computing Device 30 can have a variety of different configuration within the scope of the invention. Furthermore, it will be understood by those skilled in art that the Patient Computing Device 30 can be substituted by a PC, a smartphone, tablet PC, PDA with wireless support, and a variety of such devices that includes but are not limited to iPad, iPhone, iPod, etc., that essentially perform the functions of the Patient Computing Device 30.

Software Description

Expert System for Determining Rehab Protocol

Figure 4:
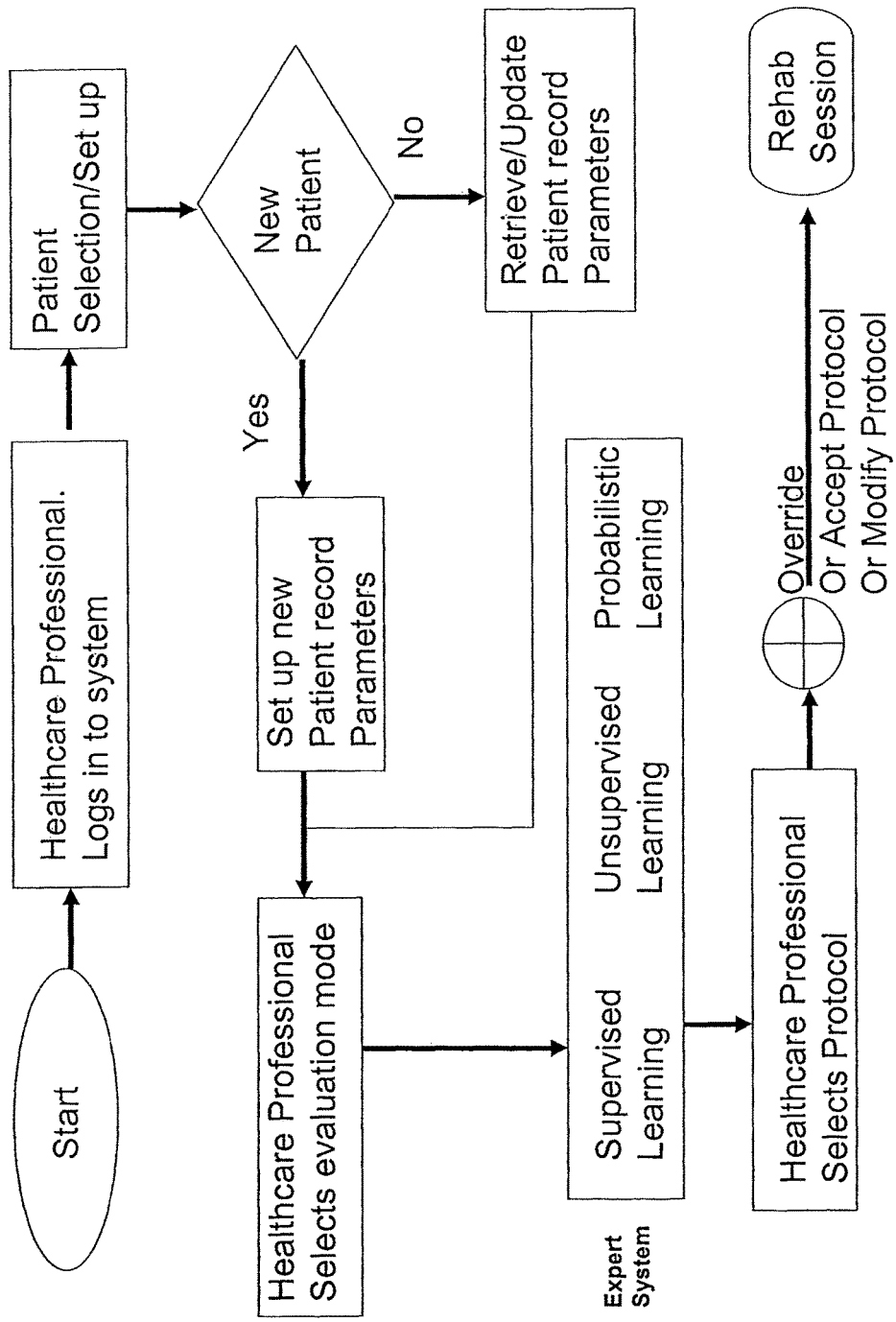
FIG. 4 is a process flow representation of the process to set up a patient for determination of rehab protocol by healthcare professional.

A typical usage scenario involves the healthcare professional inputting patient data into the system as described in FIG. 4. The healthcare professional can select one of the following evaluation methods from the expert system, namely: supervised learning, unsupervised learning, and probabilistic learning. The expert system evaluates a number of patient parameters that is input by the healthcare professional when the patient's record is created in the system.

Patient parameters include but are not limited to the following. Trunk mobility: Hip flexion, extension, abduction, adduction, int rotation, ext rotation; Knee flexion: extension, S.L.R; Ankle Dorsiflexion: Plantar flexion, inversion, eversion; Shoulder flexion: extension, abduction, int rotation, ext rotation; Elbow flexion: extension; Forearm Supine: Pronation; Wrist flexion: extension, Ulnar/Rad Dev; Finger flexion: extension; Thumb Web Space. Speed of motion, Range of motion on left side and right side as well as Pathological Synergy is evaluated and input in to the system for the above parameters.

In addition, the healthcare professional will input functional status and FIM score of the patient in to expert system of present invention. The functional status will include but are not limited to the following: Eating, Grooming, Bathing, UE Dressing, LE Dressing, Toilet Hygiene, Bed Mobility, Transfer to Bed/Chair, Transfer to Commode/Toilet, Transfer to Tub. Following balance metrics: Static sit, Dynamic sit, Static stand, Dynamic stand; Posture: Sitting, Standing; Ambulation: Level Surface, Stairs, Curbs, Ramps, Uneven Surface.

FIG. 9 captures aforementioned data points that are an input to the expert system of present invention. The healthcare professional will have a choice of determining the most optimal rehab protocol to be followed for the patient. In order to initiate the computation/evaluation by the expert system, the healthcare professional will further choose one of the following methods of determining the most optimal rehab protocol—the methods are as follows: supervised learning, unsupervised learning, and probabilistic learning. These methods of evaluation are described in detail below.

Supervised Learning

The computer uses data of the patient or the data of patients of similar prognosis, in order to decide which are the best attributes of the behavior in order to classify behaviors and to provide a mechanism for making a decision. In the case of a new patient with no prior data in the system, the expert system will leverage data sets of patients with similar conditions (prognosis) available within the system of present invention. When the system has no relevant data, an initial data set of attributes and relationships is created by the healthcare professional. As the patient uses the system, the increases in available data are leveraged by the algorithms. In particular, the methodology known as Dichotomizer 3 (ID3), first created by J. Ross Quinlan in 1975, is applicable. This methodology uses a concept known as "information gain" from the attributes of the test data. It is supervised because the "teacher" determines the attributes to examine—but not how to examine them. For example, the expert system may determine that spastic reduction of biceps and goniometric angle is important and suggest a suitable rehab protocol to the healthcare professional. In another instance the expert system may determine that finger flexion is important and suggest a suitable rehab protocol to the healthcare professional.

Unsupervised Learning

In this mode, the algorithm will be implemented as "Markov Models". (A simple but dumb example of this is for the computer to forecast weather: looking at past history of weather and its statistics—sequence of weather over many days—the computer will generate a prediction of the weather in the coming days.) Given past patient experience, the computer can create a rehab protocol. If the patient has no past experience, then the data of patients with similar prognosis will be examined by the expert system to arrive at the best predicted rehab protocol for a given patient.

Probabilistic Learning

Given patient data, the expert system can classify the current patterns by matching it to existing (past) classifications. This is represented as the "nearest neighbor" algorithm. It is good for "clustering" of responses. For example, given a set P representing patients, p1, p2, . . . pN, the nearest neighbor algorithm matches a current patient pX to the nearest neighbor in terms of rehab goals, prognoses, and available EMG response data to specific protocols. Let's suppose that the nearest neighbor algorithm determines that patient pX's closes neighbor is p2, it follows that rehab protocols suggested for patient pX mirrors that of patient p2. Healthcare professional is able to leverage this guidance along with available heuristic information and suitable adjust, modify, or adapt rehab protocol for patient pX. This methodology is used when the patient has already used the system. For a first time patient, supervised learning method is used.

It will be understood by those of ordinary skill in the art that algorithms and expert systems based on concepts of Dichotomizer3 (ID3), Markov models, and Nearest Neighbor, can be created for determination of rehab protocol in the aforementioned application in a rehabilitation setting. The choice of methodologies described here provides healthcare professional with different views of therapeutic modality and comparative measures which aid in furthering a better outcome for the patient.

A healthcare professional uses supervised learning to get the patient started on a rehab protocol using the system of present invention. The efficacy of the expert system is improved when the system has large volume of patient data for comparative purposes through computational algorithms. The healthcare professional also has the ability to override a suggested protocol or modify a suggested protocol, determined by clinical condition of the patient and other heuristic factors.

Rehab Session and Fuzzy Logic for Determining Behavior Shaping Target

Figure 5:
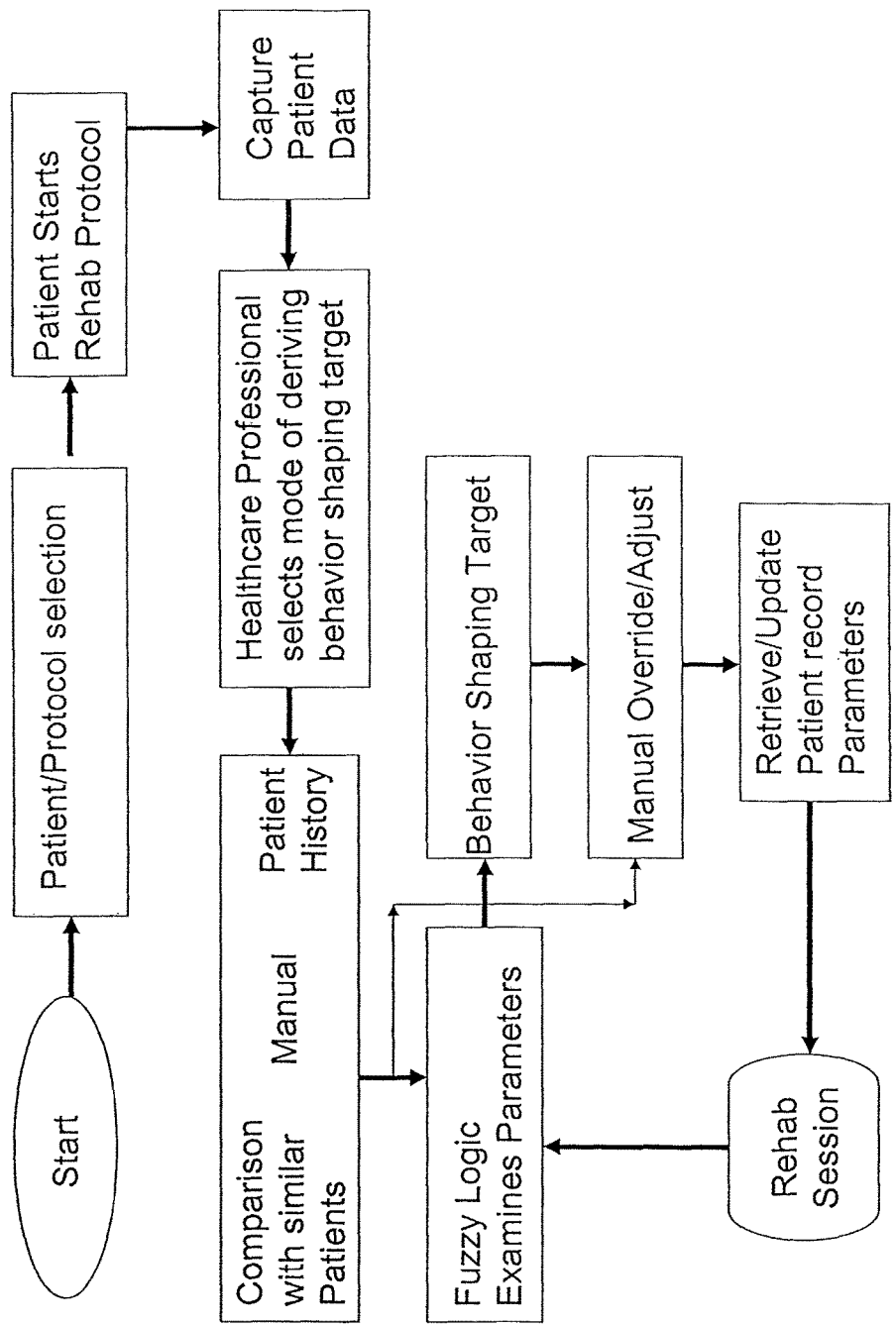
FIG. 5 is a process flow representation of the process followed by patient to undergo/follow a rehab protocol using the said system.

Once a patient starts a rehab protocol as shown in FIG. 5, a fuzzy logic algorithm examines the EMG output of the patient in near real-time conditions and dynamically adjusts the behavior shaping target. Furthermore, the fuzzy logic algorithm can also examine patient's history of progress and response to various behavior shaping targets as well as comparative data of patients with similar prognosis to dynamically derive the behavior shaping target. The near real-time boundaries are defined by the end of a single trace of EMG which constitutes a single epic. These epics constitute a predicate which is examined by the predictive algorithm to dynamically set the behavior shaping target for the patient. The healthcare professional has the option to adjust the behavior shaping target during a rehab session such that target can be more aggressive or less aggressive depending on the observations made.

A representative embodiment of patient EMG response 200 to rehab protocol is depicted in FIG. 2a. Signal 201 is a representative embodiment of a raw EMG signal—the vertical axis is graduated in $\frac{1}{100}^{th}$ units of Volts and the horizontal axis is graduated in milliseconds—$\frac{1}{1000}^{th}$ of second. A representative embodiment of rectified patient EMG response and behavior shaping target is depicted in FIG. 2b. Signal 212 is a representative embodiment of a rectified patient EMG response to a rehab protocol. 211 and 213 are representative embodiments of upper boundary and lower boundary of behavior shaping target. Neuromuscular reeducation is achieved when effort 212 coincides with behavior shaping target 211 and 213. Behavior shaping targets 211 and 213 are derived using fuzzy logic and predictive algorithms.

The system of present invention is a tool to aid a healthcare professional to provide the most optimized care for a patient. The healthcare professional therefore has the ability to override the fuzzy logic algorithm and set behavior shaping targets that are deemed to be the most optimum under given clinical conditions and patient history. The healthcare professional has the ability to manually create or custom create a behavior shaping target by observing patient's EMG response to a given protocol. Furthermore, the fuzzy logic algorithm adapts to healthcare professionals' override or modification of suggested rehab protocol by examining the recent epics as predicates.

Modes of Usage

The system of present invention lends itself for usage in a multitude of ways. The system can be used in supervised mode—in this mode, the patient undergoes rehab therapies supervised by the remote healthcare professional.

The system can be used in an unsupervised mode—in this mode, the patient is able to exercise at home or any other location unsupervised by the healthcare professional. For example, this is usually done in the intervening time between two supervised sessions.

While the system is being used in supervised mode, patient's deficit evaluation is input in to the system. Standardized indexes such as Barthel's index, Fugl Meyer, FIM scores, range of motion, speed of motion, amongst other parameters are determined and baselined for the patient for subsequent evaluation of improvement after undergoing rehab therapies. The healthcare professional has the ability to monitor progress against previous evaluation for the patient.

A healthcare professional may choose from amongst the protocol options such as supervised learning, or unsupervised learning, or probabilistic learning as presented by the expert system or choose to modify, or override and create a protocol for the patient.

While delivering therapy, therapist has the option to choose the fuzzy logic driven behavior shaping target or custom create a behavior shaping target. Furthermore, therapist has the ability to modify these options exercising judgment upon clinical observation of the patient and various other heuristic factors. The options available to a healthcare professional are as follows:

1. Patient History Based Behavior Shaping Target: Fuzzy logic algorithm evaluates/computes a behavior shaping target based on historical progress data of the patient. In this method, the software algorithms deduce the behavior shaping target by looking at the history of patient's own data from prior sessions—these include EMG data, range of motion, speed of motion, amongst other parameters such the standardized evaluation measures and baseline measures. This option presents a behavior shaping target based on patient's own historical data 2. Comparison Based Behavior Shaping Target: Fuzzy logic algorithm computes a behavior shaping target based on historical progress data of patients with similar prognosis. In this method, the fuzzy logic system compares data of the patient with the data of similar patients who have the same prognosis and therapeutic needs. If a patient p has similar prognosis as patients p1, p2, p3, pN and these patients followed rehab protocols r1, r2, r3, rN, then the system will use fuzzy logic algorithms to deduce and present a choice of behavior shaping target and associated comparative measures to the healthcare professional.

3. Manual Override: In this option, healthcare professional can manually adjust behavior target for the patient upon observing patient's EMG output.

Evidence based data influence selection of rehab protocol and treatment regimen. A representative embodiment 900, displaying efficacy 903 of rehab protocols 902 relative to patient condition 901 and patient population 904 is depicted in FIG. 10. Reference to clinical studies 905 is provided to act a reference for the healthcare professional. The value of this information presented in aforementioned format will be apparent those of skill in art.

These choices will afford the healthcare professional the ability to create a treatment approach that will most likely deliver desired outcome.

The above described embodiments are merely illustrative of the principles of the present invention. Other embodiments of the present invention will be apparent to those skilled in the art without departing from the spirit and scope of the present invention.

What is claimed is:

1. A system for treating a patient with neurological disorders of movement, comprising:
   a patient interface including: a wearable patch electromyography (EMG) sensor adapted to be worn on a body part of the patient being rehabilitated, a speed of motion sensor, a joint angle sensor and a force sensor, for detecting physiological input signals including EMG, velocity, joint angle and force;
   a healthcare computing device configured for use by a healthcare professional to assist remote patient rehabilitation by:
      receiving patient physiological input signals including near-real-time signals from said patient interface,
      automatically determining, for the patient, an initial rehab protocol based in part on said patient physiological input signals,
      receiving a user selection of a mode of deriving a visual behavior-shaping target, deriving, during a first rehabilitation session for the patient, said visual behavior shaping target based on said initial rehab protocol, said mode of deriving a visual behavior-shaping target, and said near-real-time signals from said EMG sensor,
   communicating said visual behavior shaping target to a patient computing device while the patient is undergoing rehabilitation, and
   subsequently dynamically modifying said visual behavior-shaping target during said first rehabilitation session based on said near real-time signals from said EMG sensor after the patient has reacted to said visual behavior-shaping target in said first rehabilitation session, wherein said patient interface is in wireless or wired communication with said patient computing device and wherein said healthcare computing device is in wireless or wired communication with said patient computing device.

2. The system of claim 1, wherein said healthcare computing device is configured to access a commercial or government database of health data and to use said health data in said determining of the initial rehab protocol.

3. The system of claim 1, wherein said patient interface provides tactile stimuli in response to achievement of said visual behavior-shaping target.

4. The system of claim 1, wherein said EMG sensor includes an integrated processor and signal processing hardware.

5. The system of claim 1, wherein said healthcare computing device is further configured to accept a manual input to override or adjust said initial rehab protocol in real-time.

6. The system of claim 1, wherein said mode of deriving a visual behavior-shaping target consists of either a manual mode, a mode based on patient history, or a mode based on similar patients.

7. The system of claim 6, wherein said mode based on similar patients is based on historical progress data of said similar patients.

8. The system of claim 1, further comprising said healthcare computing device determining said visual behavior-shaping target for a second rehabilitation session based on the patient's EMG signals from a previous rehabilitation session.

9. The system of claim 1, wherein said visual behavior shaping target is displayed to the patient along with an avatar of the body part being rehabilitated.

10. The system of claim 1,
wherein said subsequent dynamic modification of said visual behavior-shaping target is also based on speed of motion of the body part being rehabilitated and inputs from said joint angle and force sensors.

11. The system of claim 10, wherein said visual behavior-shaping target is displayed to the patient along with an avatar of the body part being rehabilitated.

12. The system of claim 1, wherein said visual behavior-shaping target comprises a graph showing past actual patient performance, past target levels, current patient performance and current target levels.

13. The system of claim 1, further comprising a second EMG sensor and wherein said visual behavior-shaping target is determined at least in part based on EMG signals from agonist and antagonist muscle groups of the patient body part being rehabilitated.

14. A system for treating a patient with neurological disorders of movement, comprising:
a patient interface including a wearable patch electromyography (EMG) sensor adapted to be worn on a body part of the patient, said body part being rehabilitated;
a healthcare computing device configured for use by a healthcare professional to assist remote patient rehabilitation by:
receiving patient physiological input signals including near-real-time signals from said EMG sensor,
automatically determining, for the patient, an initial rehab protocol based in part on said patient physiological input signals,
receiving a user selection of a mode of deriving a visual behavior-shaping target,
deriving, during a first rehabilitation session for the patient, said visual behavior shaping target based on said initial rehab protocol, said mode of deriving a visual behavior-shaping target, and said near-real-time signals from said EMG sensor,
communicating said visual behavior shaping target to a patient computing device while the patient is undergoing rehabilitation, and
subsequently dynamically modifying said visual behavior-shaping target during said first rehabilitation session based on said near real-time signals from said EMG sensor after the patient has reacted to said visual behavior-shaping target in said first rehabilitation session,
wherein said EMG sensor is in wireless or wired communication with said patient computing device and wherein said healthcare computing device is in wireless or wired communication with said patient computing device
the system further comprising
a speed of motion sensor adapted for sensing speed of motion of said body part and wherein said dynamic adjustment of said visual behavior-shaping target is also based on sensed speed of motion of said body part.

15. The system of claim 14, wherein said visual behavior-shaping target is further determined based on speed of motion of the body part being rehabilitated.

16. A system for treating a patient with neurological disorders of movement, comprising:
a patient interface including first and second wearable patch electromyography (EMG) sensors, a speed of motion sensor, a joint angle sensor, and a force sensor adapted to be worn on a body part of the patient, said body part being rehabilitated;
a healthcare computing device configured for use by a healthcare professional to assist remote patient rehabilitation by:
receiving patient physiological input signals including near-real-time signals from said first and second EMG sensors, said speed of motion sensor, said joint angle sensor, and said force sensor,
determining, for the patient, an initial rehab protocol based in part on said patient physiological input signals,
receiving a user selection of a mode of deriving a visual behavior-shaping target,
deriving, during a first rehabilitation session for the patient, said visual behavior-shaping target based on said initial rehab protocol, said mode of deriving a visual behavior-shaping target, and said near-real-time signals from said first and second EMG sensors,
communicating said visual behavior-shaping target to a patient computing device while the patient is undergoing rehabilitation, and
subsequently dynamically modifying said visual behavior-shaping target during said first rehabilitation session based on said near real-time signals from said first and second EMG sensors, speed of movement of the body part being rehabilitated and inputs from said joint angle and force sensors, after the patient has reacted to said visual behavior-shaping target in said first rehabilitation session,
wherein said first and second EMG sensors are configured to produce signals from agonist and antagonist muscle groups of the patient body part being rehabilitated and are in wireless or wired communication with said patient computing device, wherein said healthcare computing device is in wireless or wired communication with said patient computing device, and wherein said visual behavior-shaping target is displayed on said patient computing device along with an avatar of the body part being rehabilitated.

17. The system of claim 16, wherein said healthcare computing device is further configured to base said dynamic modifying of a visual behavior-shaping target in part on historical progress data of the patient being rehabilitated.

18. The system of claim 16, wherein said healthcare computing device is further configured to base said dynamic modifying of a visual behavior-shaping target in part on historical progress data of patients with similar prognoses as the patient being rehabilitated.

* * * * *